(12) United States Patent
Stumpe et al.

(10) Patent No.: US 7,825,268 B2
(45) Date of Patent: Nov. 2, 2010

(54) ALKOXYLACTONES, ALKOXYLACTAMS AND ALKOXYTHIOLACTAMS FOR CONTROLLING PROCESSES BASED ON MICROBIAL INTERACTION

(75) Inventors: Stefan Stumpe, Düsseldorf (DE); Roland Breves, Mettmann (DE); Ursula Huchel, Köln (DE); Frank Janssen, Düsseldorf (DE); André Hätzelt, Düsseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 1009 days.

(21) Appl. No.: 11/473,795

(22) Filed: Jun. 22, 2006

(65) Prior Publication Data

US 2008/0207734 A1    Aug. 28, 2008

Related U.S. Application Data

(63) Continuation of application No. PCT/EP2004/014141, filed on Dec. 11, 2004.

(30) Foreign Application Priority Data

Dec. 23, 2003   (DE) ............................... 103 61 457

(51) Int. Cl.
A61K 31/4015   (2006.01)
A61K 31/341    (2006.01)
C07D 207/26    (2006.01)
C07D 307/33    (2006.01)

(52) U.S. Cl. .................. 549/477; 514/425; 514/473; 548/544

(58) Field of Classification Search .................. None
See application file for complete search history.

(56) References Cited

U.S. PATENT DOCUMENTS

| 3,547,828 | A  | 12/1970 | Mansfield |
| 3,707,535 | A  | 12/1972 | Lew |
| 3,772,269 | A  | 11/1973 | Lew |
| 3,839,318 | A  | 10/1974 | Mansfield |
| 4,349,669 | A  | 9/1982  | Klahr |
| 5,705,169 | A  | 1/1998  | Stein |
| 5,730,960 | A  | 3/1998  | Stein |
| 6,001,600 | A  | 12/1999 | Hodgson |
| 6,287,836 | B1 | 9/2001  | Brown |

FOREIGN PATENT DOCUMENTS

| DE | 1 165 574 | 3/1964 |
| DE | 19 43 689 | 3/1970 |
| DE | 20 36 472 | 2/1971 |
| DE | 2 024 051 | 12/1971 |
| DE | 30 01 064 | 7/1981 |
| DE | 197 12 033 | 9/1998 |
| EP | 0 077 167 | 4/1983 |
| EP | 0 693 471 | 1/1996 |
| EP | 0 694 521 | 1/1996 |
| EP | 0 818 450 | 1/1998 |
| EP | 0 881 297 | 12/1998 |
| EP | 0 909 820 | 4/1999 |
| FR | 2 252 840 | 6/1975 |
| GB | 1 333 475 | 10/1973 |
| GB | 1 494 915 | 12/1977 |
| GB | 1 494 916 | 12/1977 |
| WO | WO 96/29392 | 9/1996 |
| WO | WO 00/56154 | 9/2000 |
| WO | WO 01/49708 | 7/2001 |
| WO | WO 01/68090 | 9/2001 |
| WO | WO 01/68091 | 9/2001 |
| WO | WO 01/76594 | 10/2001 |
| WO | WO 01/85664 | 11/2001 |
| WO | WO 01/94543 | 12/2001 |
| WO | WO 02/16623 | 2/2002 |

(Continued)

OTHER PUBLICATIONS

Ishii et al., "Regio- and Stereoselective Dehydrogenation of α,ω-Diols Catalyzed by a Rhodium Hydride Complex" Journal of Organic Chemistry (1986) vol. 51 No. 14 pp. 2822-2824.*

(Continued)

Primary Examiner—Eric S Olson
(74) Attorney, Agent, or Firm—David P. LeCroy

(57) ABSTRACT

Compounds of the Formula I,

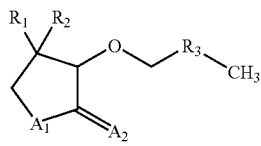

wherein $A_1$ is O or NH; $A_2$ is O or S; each of $R_1$ and $R_2$ is independently hydrogen, a methyl or $C_2$-$C_8$-saturated or mono- or doubly unsaturated, branched or linear hydrocarbon group; and $R_3$ is a $C_1$-$C_{18}$-saturated or mono- or doubly unsaturated, branched or linear hydrocarbon group wherein, each of $R_1$, $R_2$ and $R_3$ comprises a heteroatom selected from the group consisting of O and S in the chain and/or is mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl are useful for controlling the interaction process between microorganisms such as in the development and/or maturation of biofilms; multicellular swarm behavior; the concerted development of antibiotic resistances; the concerted synthesis of antibiotics; the concerted synthesis of pigments; the concerted production of extracellular enzymes; or the concerted production of virulence factors.

13 Claims, 2 Drawing Sheets

FOREIGN PATENT DOCUMENTS

WO      WO 02/47681      6/2002

OTHER PUBLICATIONS

Figure 1:
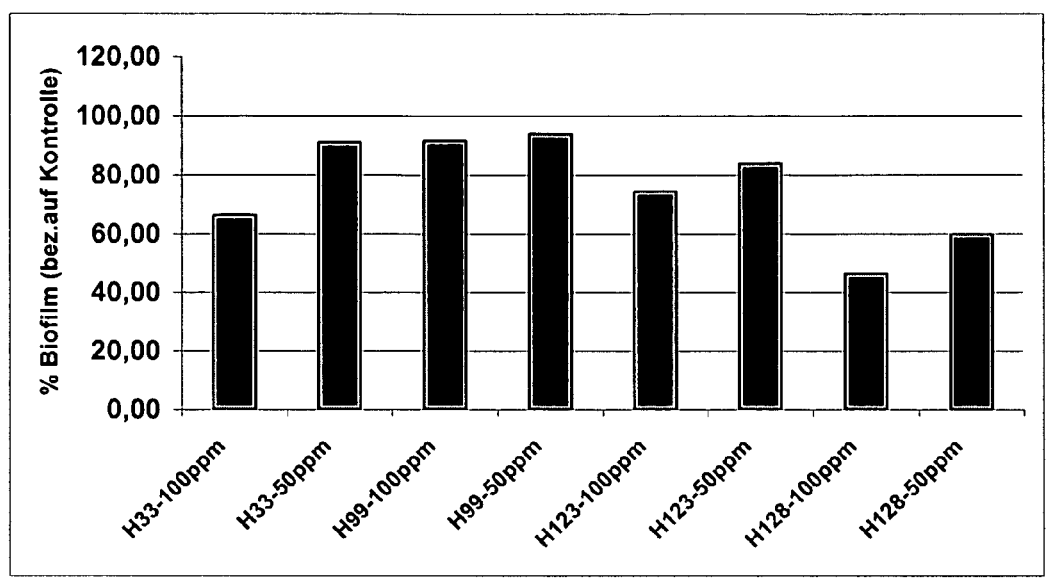

Sakuragi et al., "The Synthesis of Long Chain Fatty Acid Derivatives of Pantothenic Acid" Journal of the American Chemical Society (1956) vol. 78, pp. 838-839.*

Akbutina et al., "Chiral synthetic block based on (R)-pantolactone" Mendeleev Communications (2003) vol. 13 No. 3, pp. 151-152.*

Kitano et al., "Thermal intramolecular cycloaddition of 4-alkenylfulvene; highly regio- and diastereoselective formation of [4+2] adduct" Tetrahedron (2003) vol. 59 pp. 2673-2677.*

Patent abstracts of Japan, vol. 017, No. 119, (C-1034) & JP 04 300877A (publication number), publication date: Oct. 23, 1992.

Daremon, C., et al., "Obtention et etude de quelques gamma-butanolides . . . ," Bulletin de la societe chimique de France, pp. 294-301, XP009046464, (1971).

Miller, M.B., et al., "Quorum sensing in bacteria," Annu. Rev. Microbiol., 55:165-199, (2001).

Kleerebezem, M., et al., "Peptide pheromone-dependent regulation of antimicrobial peptide production in Gram-positive bacteria . . . ," Peptides, 22:1579-1596, (2001).

Greenberg, E.P., "Quorum sensing in Gram-negative bacteria," ASM News, 63:371-377, (1997).

Chang, C., "The two-component system. Regulation of diverse signaling pathways in prokaryotes and eukaryotes," Plant Physiol., 117:723-731, (1998).

Eberl, L., "N-acyl homoserinelactone-mediated gene regulation in gram-negative bacteria," Syst. Appl. Microbiol., 22:493-506, (1999).

Michael, B., et al., "SdiA of *Salmonella enterica* is a LuxR homolog that detects mixed microbial communities," J. Bacteriol., 183:5733-5742, (2001).

Gray, K.M., et al., "The evolution of bacterial LuxI and LuxR quorum sensing regulators," Microbiology, 147(Pt. 8):2379-2387, (2001).

Zhang, R.G., et al., "Structure of a bacterial quorum-sensing transcription factor complexed with pheromone and DNA," Nature, 417:971-974, (2002).

Dong, Y.H., et al., "Quenching quorum-sensing-dependent bacterial infection by an N-acyl homoserine lactonase," Nature, 411:813-817, (2001).

Manefield, M., et al., "Evidence that halogenated furanones from *Delisea pulchra* inhibit acylated homoserine lactone . . . ," Microbiology, 145(Pt.2):283-291, (1999).

Bryers, J.D., "Gene therapy approach to preventing bacterial colonization of biomaterials," Abstract of papers, 222nd ACS National Meeting, (2001).

Todd, C., et al., "Volatile silicone fluids for cosmetic formulations," Cosm. Toil., 91:29-32, (1976).

Lochhead,R., ed., "Encyclopedia of Polymers and Thickeners for Cosmetics," Cosm. Toil., 108:95-135, (1993).

Finkel, P., "Formulierung kosmetischer Sonnenschutzmittel," SOFW-Journal, 122:543-548, (1996). Also see English abstract on p. 543.

"Kosmetische Farbemittel," Farbstoffkommission der Deutschen Forschungsgemeinschaft, Verlag Chemie, Weinheim, pp. 81-106, (1991).

* cited by examiner

ALKOXYLACTONES, ALKOXYLACTAMS AND ALKOXYTHIOLACTAMS FOR CONTROLLING PROCESSES BASED ON MICROBIAL INTERACTION

CROSS REFERENCE TO RELATED APPLICATIONS

This application is a continuation under 35 U.S.C. §365(c) and 35 U.S.C. §120 of International Application PCT/EP2004/014141, filed Dec. 11, 2004. This application also claims priority under 35 U.S.C. §119 of German Application DE 103 61 457.5, filed Dec. 23, 2003. Each application is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION.

(1) Field of the Invention

The present invention relates to novel alkoxylactones, alkoxylactams and alkoxythiolactams, to methods for controlling processes based on microbial interaction using said alkoxylactones, alkoxylactams and alkoxythiolactams, to uses of said alkoxylactones, alkoxylactams and alkoxythiolactams, and to agents containing said alkoxylactones, alkoxylactams and alkoxythiolactams.

Microorganisms communicate with each other by means of a plurality of different signals. In particular, the mechanisms of communication and interaction of bacteria are extensively described in the prior art.

Specific histidine kinases or homologous proteins that are intended for use in screening for antibacterial substances are described in the documents WO 00/56154; EP 0881297; U.S. Pat. No. 6,287,836; EP 0909820 and U.S. Pat. No. 6,001,600. The kinases derive exclusively from gram-positive organisms.

In WO 01/49708, a peptide with at least 6 but less than 200 amino acids is used for blocking a response regulator. However, no signal molecules are blocked, rather the activation of the next protein in the signal chain is inhibited.

The formation of mature biofilms by or with bacteria is dependent on the communication between bacterial cells over various extracellular signal substances.

Depending on the cell count density of the adhering bacteria, any level of this messenger substance above a minimum concentration effects an activation of the biofilm formation as well as inducing additional virulent genes. This phenomenon is called "Quorum Sensing" and fundamentally opens up the possibility of controlling biofilms, without destroying the living germs in the biofilm.

(2) Description of Related Art, Including Information Disclosed Under 37 C.F.R. §§1.97 and 1.98.

Up to now, a great many signal molecules have been identified in gram negative and gram-positive germs [Miller, M. B., Bassler, B. L. (2001) Quorum sensing in bacteria. Annu Rev Microbiol. 55, 165-199; Kleerebezem, M., Quadri, L. E. (2001) Peptide pheromone-dependent regulation of antimicrobial peptide production in Gram-positive bacteria: a case of multicellular behavior. Peptides 22, 1579-1596].

The structure of these signal molecules has been particularly well investigated for gram-negative organisms. The signal substances (pheromones) found in these organisms are often members of a group of different N-acyl-L-homoserine lactones (AHL) that differ in the length of the N-acyl side groups and by modifications at the C3 position (3-oxo or 3-hydroxy groups) [Greenberg, E. P. (1997) Quorum sensing in Gram-negative bacteria. ASM News 63, 371-377].

The mechanisms are not yet as well understood for gram-positive bacteria. Often, smaller peptides are described as the signal molecules. [Kleerebezem, M., Quadri, L. E. (2001) Peptide pheromone-dependent regulation of antimicrobial peptide production in Gram-positive bacteria: a case of multicellular behavior. Peptides 22, 1579-1596].

However, the fundamental principle is similar. Each signal molecule is recognized and bound by specific, generally membrane-bound cellular receptors (two component systems).

In gram-negative bacteria, specific histidine kinases inter alia act as the implied receptors. These histidine kinases are constituents of the so-called two-component system. The second component is formed by the so-called response regulator. When a signal molecule binds to such a histidine kinase, the response regulator is activated by it. The activated response regulator acts itself as the activator of many different cellular processes [Chang C, Stewart, The two-component system. Regulation of diverse signaling pathways in prokaryotes and eukaryotes. Plant Physiol. 1998 Jul; 117(3):723-31.]

Whereas there are a large number of such two-component systems with the most varied functions in all cells, intracellular transcription-activator-proteins ("LuxR-proteins") are mainly responsible for the biofilm development by gram-negative bacteria. Due to their functionality, the proteins of the LuxR class are firstly able to bind AHLs, but secondly also to undergo interactions with regulation areas of DNA molecules. [Eberl L, N-acyl homoserinelactone-mediated gene regulation in gram-negative bacteria, Syst Appl Microbiol. 1999 Dec; 22(4):493-506; Michael B, Smith J N, Swift S, Heffron F, Ahmer B M. SdiA of *Salmonella enterica* is a LuxR homolog that detects mixed microbial communities. J Bacteriol. 2001 Oct; 183(19):5733-42; Gray K M, Garey J R., The evolution of bacterial LuxI and LuxR quorum sensing Microbiology. 2001 Aug; 147(Pt 8):2379-87.].

Recently, it is known that only the N-terminal part of the transcription activator protein (ca. 200 amino acids) is responsible for binding the AHL molecule. [Zhang R G, Pappas T, Brace J L, Miller P C, Oulmassov T, Molyneaux J M, Anderson J C, Bashkin J K, Winans S C, A., Structure of a bacterial quorum-sensing transcription factor complexed with pheromone and DNA. Nature. 2002 Jun 27; 417(6892): 971-4.].

From the prior art and science, essentially three different concepts are described for biofilm prevention or control.

1. Cleavage of the Messenger Substances by Enzymes, e.g., Lactonases.

Recently, various enzymes have been isolated from gram-positive bacillae, which specifically cleave the AHL molecule and can thereby switch off these signal paths ("Quorum quenching"). These lactonases have been described many times [Dong Y H, Wang L H, Xu J L, Zhang H B, Zhang X F, Zhang L H. (2001) Quenching quorum-sensing-dependent bacterial infection by an N-acyl homoserine lactonase. Nature. 411, 813-817; WO 0185664; WO 0216623].

2. Blocking/Binding of Messenger Substances per se, e.g., with Antibodies.

A further possibility to prevent biofilms is the use of AHL-specific antibodies. By binding an antibody of this type to the messenger substance, the latter is no longer able to bind to its original receptor (=histidine kinase) [WO 0194543]. However, due to the high costs to manufacture the antibody, this method is at most feasible for medical purposes.

3. Blocking the Cellular Receptors of the Messenger Substances, e.g., by Means of Structurally Analogous Substances.

Furanones and furanone derivatives are particularly known as structurally analogous substances. [Manefield M, de Nys R, Kumar N, Read R, Givskov M, Steinberg P, Kjelleberg. Evidence that halogenated furanones from *Delisea pulchra* inhibit acylated homoserine lactone (AHL)-mediated gene expression displacing the AHL signal from its receptor protein. Microbiology. 1999 Feb; 145 (Pt 2):283-91; WO 9629392; WO 0168091; WO 0168090; WO 0176594].

Furanones illustrate AHL analogues in terms of their structure. They interrupt the signal transmission path, in that they competitively suppress the AHL signal substances and bind to the intracellular target molecule (intracellular transcription activator protein). The growth of the affected germs is not inhibited at low concentrations by the effect of the furanone.

Besides the addition of furanones, the use of antibodies or antibody fragments has also been discussed in individual cases. [Bryers, J. D., 2001, Gene therapy approach to preventing bacterial colonization of biomaterials, Abstracts of papers, 222nd ACS National Meeting].

The present invention is based on the problem of providing novel substances by means of which the interaction of microbes with one another can be controlled and regulated.

BRIEF SUMMARY OF THE INVENTION

The present invention pertains to a compound of Formula I,

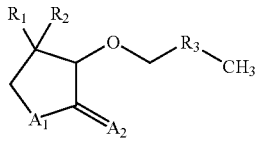

I wherein $A_1$ is O or NH; $A_2$ is O or S; each of $R_1$ and $R_2$ is independently hydrogen, a methyl or $C_2$-$C_8$-saturated or mono- or doubly unsaturated, branched or linear hydrocarbon group; and $R_3$ is a $C_1$-$C_{18}$-saturated or mono- or doubly unsaturated, branched or linear hydrocarbon group wherein, each of $R_1$, $R_2$ and $R_3$ comprises a heteroatom selected from the group consisting of O and S in the chain and/or is mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl. The compounds according to the invention are useful for controlling the interaction process between microorganisms such as in the development and/or maturation of biofilms; multicellular swarm behavior; the concerted development of antibiotic resistances; the concerted synthesis of antibiotics; the concerted synthesis of pigments; the concerted production of extracellular enzymes; or the concerted production of virulence factors.

BRIEF DESCRIPTION OF THE SEVERAL VIEWS OF THE DRAWING(S)

FIG. 1. Effect of various alkoxylactones on the biofilm formation of *P. aeruginosa*. The data refer to the control without active substance (=100%).

Figure 2:
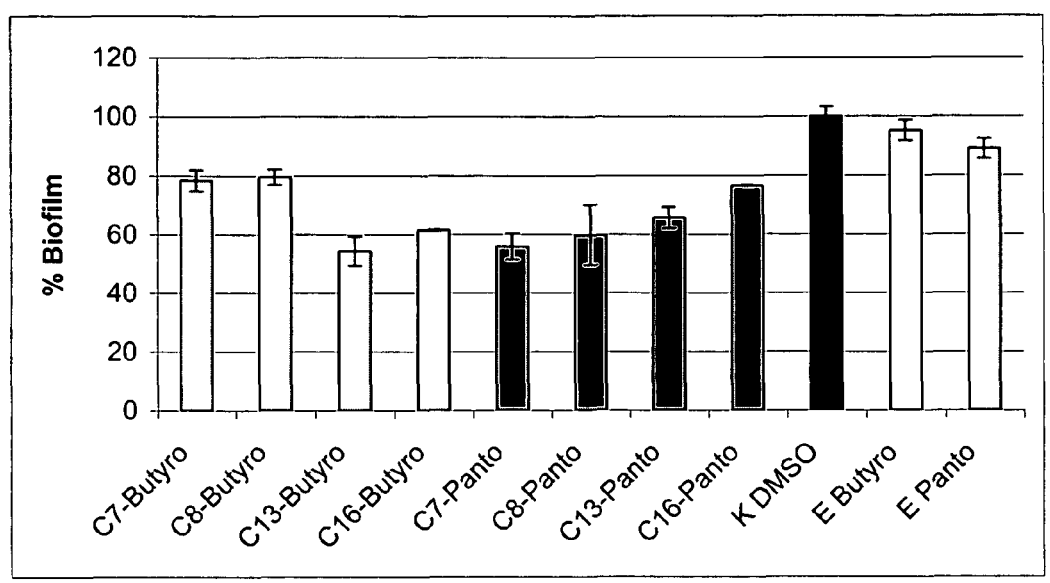

FIG. 2: Effect of the side chains of alkoxylactones on the biofilm formation of *P. aeruginosa* (black: DMSO-Control; light gray: Butyrolactone derivatives; dark gray: Pantolactone derivatives; hatched: Educts Hydroxybutyrolactone and Pantolactone)

DETAILED DESCRIPTION OF THE INVENTION

According to the invention, the compounds of Formula I that are particularly preferred are a-octyloxypantolactone, a-octyloxybutyrolactone, a-tridecyloxybutyrolactone, a-hexadecyloxybutyrolactone, a-heptyloxypantolactone, a-tridecyloxypantolactone and a-hexadecyloxypantolactone.

The hydrocarbon groups of the compound according to Formula I, and independently of one another the groups $R_1$, $R_2$ and $R_3$ can also optionally comprise a heteroatom selected from O and S in the chain and/or be mono- or multiply, preferably singly substituted, in particular, by groups selected from halogen, in particular, fluorine, chlorine or bromine, hydroxy, $C_1$-$C_6$-alkyl, particularly $C_1$-$C_4$-alkyl, trifluoromethyl, $C_1$-$C_6$-alkoxy, particularly $C_1$-$C_4$-alkoxy, preferably methoxy or ethoxy, $C_6$-$C_{10}$-aryl, particularly $C_6$-aryl, preferably phenyl, and $C_1$-$C_6$-alkyl-$C_6$-$C_{10}$-aryl, particularly $C_1$-$C_4$-alkyl-$C_6$-aryl, preferably toluyl.

Preferably, $A_1$ and $A_2$ stand for O, $R_1$ and $R_2$ stand for hydrogen or methyl, and $R_3$ stands for butylene, pentylene, hexylene, heptylene, octylene, nonylene, decylene, undecylene, dodecylene, tridecylene or tetradecylene. In a particularly preferred embodiment, $R_1$ and $R_2$ stand for hydrogen or methyl, and $R_3$ stands for decylene, undecylene, dodecylene, tridecylene or tetradecylene. In a further particularly preferred embodiment, $R_1$ and $R_2$ stand for methyl and $R_3$ for butylene, pentylene, hexylene, heptylene or octylene. Most preferred compounds are those in which $A_1$ and $A_2$ are not simultaneously O and $R_1$ and $R_2$ are not simultaneously hydrogen and methyl and $R_3$ is not methylene or ethylene.

The inventive compounds can be present in the form of their racemates or in the form of their isolated stereoisomers and/or enantiomers.

The inventive compounds can be advantageously prepared by the reaction of the appropriate lactone, lactam or thiolactam with a 1-haloalkane, particularly 1-chloroalkane, 1-bromoalkane or 1-iodoalkane, particularly preferably 1-bromoalkane, in a suitable organic solvent (e.g. dimethylformamide) in the presence of a suitable base, particularly cesium carbonate or cesium halide.

According to the invention, compounds in which $R_3$ is a heptylene group or a shorter group, can be worked up by distillation from the reaction mixture. When $R_3$ is a larger group, the work up is preferably effected by crystallization.

The preparative method can be suitably modified by the person skilled in the art as a function of the size and type of the desired target compound.

A further subject matter of the present invention is a method for controlling processes based on microbial interaction, wherein, (a) where necessary the interacting microorganisms are determined,
(b) where necessary the appropriate compound or appropriate compounds are selected from the inventive compounds, and
(c) the inventive compounds are added in amounts sufficient for the desired control to the medium in which the microbial interaction takes place.

Particularly suitable microorganisms are selected from *Aeromonas hydrophila, Aeromonas salmonicida, Agrobacterium tumefaciens, Burkholderia cepacia, Chromobacterium violaceum, Enterobacter agglomerans, Erwinia carotovora, Erwinia chrysanthemi, Escherichia coli, Nitrosomona europaea, Obesumbacterium proteus, Pantoea stewartii, Pseudomonas aeruginosa, Pseudomonas aureofaciens, Pseudomonas fluorescens, Pseudomonas syringae, Ralstonia solanacearum, Rhizobium etli, Rhizobium leguminosarum, Rhodobacter sphaeroides, Salmonella enterica, Serratia liquefaciens, Vibrio anguillarum, Vibrio fischeri, Xenorhabdus nematophilus, Yersinia enterolytica, Yersinia pestis, Yersinia pseudotuberculosis* and *Yersinia ruckeri*.

According to the invention, gram-positive bacteria are also suitable microorganisms.

The most important are germs that particularly in aqueous solutions are strongly involved in the biofilm development. These are primarily germs from the large group of pseudomonads, particularly *P. aeruginosa, Burkholderia cepacia, Serratia, Rhizobium, E. coli*. Further important biofilm germs are aquabacterium and xanthomonas.

In most cases the bacterial communication system do not govern morphological changes of individual cells but influence the pathogenicity of each organism. Some of the most significant functions of this communication system are listed as examples below:

Regulation of the expression of the bioluminescence gene (e.g. *Photobacterium fischeri*)
Production of the β-lactam-antibiotic Carbapenem (*Erwinia carotovora*) and AB-production in *Pseudomonas aureofaciens*
Conjugative plasmid transfer (traI/traR from *Agrobacterium tumefaciens*),
Starvation response (e.g. *Pseudomonas*)
Bacterial locomotion (swrI/swrR from *Serratia liquefaciens*) and by *P. aeruginosa*
Development of differentiated biofilms (*P aeruginosa, B. cepacia*)
Production of different virulence factors (cell associated virulence factors by *P. aeruginosa*, e.g. extracellular factors, such as proteases (LasB-elastase, alkaline protease and LasA-protease), haemolysine (rhamnolipid and phosoholipase) and toxins (exotoxin A and exoenzyme S)
Interspecific cell-cell cross-talk between different bacterial species e.g. between *P. cepacia* and *P. aeruginosa*

The regulation of the production of virulence factors plays a particular role with *pseudomonas aeruginosa* and *burkholderia cepacia* in conjunction with the chronic infection of cystic fibrosis patients.

According to the invention, the microbial interaction is selected from the development and/or maturation of biofilms, multicellular swarm behavior, the concerted development of antibiotic resistances, the concerted synthesis of antibiotics, the concerted synthesis of pigments, the concerted production of extracellular enzymes, in particular, hydrolytic enzymes, and the concerted production of virulence factors, preferably the development and/or maturation of biofilms.

A further subject matter of the invention is the use of the inventive compounds for controlling processes based on microbial interaction, especially for controlling the development and/or maturation of biofilms, particularly preferably of biofilms in which are involved gram-negative bacteria.

For example, ship hulls can be protected in this way against algae growth. The biofilm forms the basis for the settlement of larger organisms such as mussels and algae. This growth, due to its viscous drag, slows down the ship and thereby leads to an increased fuel consumption, as a result of which the deposits have to be periodically removed at great expense.

Advantageously, the inventive compounds, in contrast to antibiotics, do not kill off the bacteria, but only inhibit their communication system such that the development of a mature, mucous does not occur. It is particularly advantageous that the microorganisms cannot develop any resistance against these compounds that represent structural analogs of the AHL molecules used by the microorganisms themselves.

Medically relevant biofilms are a particularly preferred object of the present invention. The following may be cited in particular:

Cystic fibrosis: The chronic lung infection that affects cystic fibrosis patients is caused by the gram-negative rod-shaped bacterium *Pseudomonas aeruginosa*. Once a biofilm has formed in the lungs, the bacteria can no longer be destroyed, even by the most aggressive antibiotic treatment. Due to a defective salt transport in the epithelial cells, patients with this hereditary disease develop viscous mucus in the lungs, which forms a good nutritive medium for pathogens.

Contact lenses: Film-forming bacteria can also establish themselves on contact lenses. Most notably, the germ *Pseudomonas aeruginosa* plays an important role. Although it does not occur in the normal flora of the eye, it can attain the eye from mascara sponges or contaminated cleaning solutions for contact lenses. Corneal inflammations often occur even from only small lesions.

Implants: Bacterial biofilms are responsible for about 60 percent of all infections in implantation surgery. The mortality of the patients is particularly high in the case of endogenic implants such as synthetic joints or heart valves.

Catheters: Intravenous accesses, as can be required for blood transfusions or synthetic nutrition, can also lead to severe infections. Germs from the normal skin flora, such as staphylococcus types, or pathogens, such as various species of pseudomonas, can accumulate on the external side of the access, prior to being carried into the blood vascular system of the patient. The bacteria then create a film that when removed can trigger chronic infections.

Dental plaque: Plaque on teeth is not only unattractive but also dangerous in certain circumstances. Caries, gingivitis (bleeding of the gum) and paradentitis (inflammation of the gum) can result. Moreover, the germs from the mouth flora can enter the blood circulation through small lesions and are suspected of causing heart attacks, premature births or diabetes.

Preferably the use according to the invention is accordingly effected in sterilization agents, disinfectants, impregnation agents or preservatives, detergents or cleansing agents, or in coolants or cooling lubricants (technical application solutions) as well as in the field of water purification/water treatment, and the pharmaceutical, food, brewing, medical, colorant, wood, textile, cosmetic, leather, tobacco, hide, rope, paper, pulp, plastic, fuel, oil, rubber or machine industries.

Particularly preferably, the inventive use is for biofilm control for medical equipment, instruments and apparatuses, particularly for catheters and endoscopes.

Further subject matters of the present invention are body care agents, hair shampoos, hair care agents, bubble baths, shower baths, creams, gels, lotions, alcoholic and aqueous-alcoholic solutions, emulsions, wax/fatty masses, stick preparations, powders or salves, mouth-, tooth- or denture care products, cosmetics, detergents, cleansing agents, rinsing agents, hand detergents, hand dishwashing agents, automatic dishwasher agents, disinfectants and agents for treating foodstuffs, pharmaceuticals, filter media, textiles, hides, paper, skins or leather, which comprise compounds according to the invention.

The shampoos and/or hair care products as well as bubble baths, shower baths, creams, gels, lotions, alcoholic and aqueous-alcoholic solutions, emulsions, wax/fatty masses, stick preparations, powders or salves that include inventive compounds, can comprise mild surfactants, oils, emulsifiers, greases, pearlescent waxes, consistence providers, thickeners, polymers, silicone compounds, fats, waxes, stabilizers, biogenetic active principles, deodorants, antiperspirants, anti-dandruff agents, film formers, swelling agents, UV-light protection factors, antioxidants, hydrotropes, preservatives, insect repellants, sun tans, solubilizers, perfume oils, colorants and the like as auxiliaries and additives.

Typical examples of suitable mild, i.e. particularly skin-compatible surfactants are fatty alcohol polyglycol ether sulfonates, monoglyceride sulfates, mono and/or dialkyl sulfosuccinates, fatty acid isethionates, fatty acid sarcosinates, fatty acid taurides, fatty acid glutamates, a-olefin sulfonates, ether carboxylic acids, alkyl oligo glucosides, fatty acid glucamides, alkylamidobetaines and/or protein-fatty acid condensates, the last preferably on the basis of wheat proteins.

The following can be considered as oils, for example: Guerbet alcohols based on fatty alcohols with 6 to 18, preferably 8 to 10 carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, such as for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition, suitable esters are esters of linear $C_6$-$C_{22}$-fatty acids with branched alcohols, especially 2-ethylhexanol, esters of hydroxycarboxylic acids with linear or branched $C_6$-$C_{22}$-fatty alcohols, especially dioctyl malate, esters of linear and/or branched fatty acids with polyhydroxy alcohols (e.g. propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, especially benzoic acid, esters of $C_2$-$C_{12}$-dicarboxylic acids with linear or branched alcohols with 1 to 22 carbon atoms or polyols with 2 to 10 carbon atoms and 2 to 6 hydroxyl groups, vegetal oils, branched primary alcohols, substituted cyclohexanes, linear and branched $C_6$-$C_{22}$-fatty alcohol carbonates, Guerbet carbonates, esters of benzoic acid with linear and/or branched $C_6$-$C_{22}$-alcohols (e.g. Finsolv® TN), linear or branched, symmetrical or unsymmetrical dialkyl ethers with 6 to 22 carbon atoms per alkyl group, ring-opened products of epoxidized fatty acid esters with polyols, silicone oils and/or aliphatic or naphthenic hydrocarbons, such as, for example, squalane, squalene or dialkylcyclohexanes.

Emulsifiers can be selected, for example, from nonionic surfactants from at least one of the following groups:
(1) Addition products of 2 to 30 moles ethylene oxide and/or 0 to 5 moles propylene oxide to linear fatty alcohols with 8 to 22 carbon atoms, to fatty acids with 12 to 22 carbon atoms, to alkyl phenols with 8 to 15 carbon atoms in the alkyl group as well as alkylamines with 8 to 22 carbon atoms in the alkyl group;
(2) $C_{12/18}$-fatty acid mono and diesters of addition products of 1 to 30 moles ethylene oxide on glycerin;
(3) Glycerin mono and diesters and sorbitol mono and diesters of saturated and unsaturated fatty acids with 6 to 22 carbon atoms and their ethylene oxide addition products;
(4) Alkyl- and/or alkenyl mono and -oligoglycosides with 8 to 22 carbon atoms in the alk(en)yl group and their ethoxylated analogs;
(5) Addition products of 15 to 60 moles ethylene oxide on castor oil and/or hydrogenated castor oil;
(6) Polyol esters and especially polyglycerin esters;
(7) Addition products of 2 to 15 moles ethylene oxide on castor oil and/or hydrogenated castor oil;
(8) Partial esters based on linear, branched, unsaturated or saturated $C_{6/22}$-fatty acids, ricinoleic acid as well as 12-hydroxystearic acid and glycerin, polyglycerin, pentaerythritol, dipentaerythritol, sugar alcohols (e.g. sorbitol), alkyl glucosides (e.g. methyl glucoside, butyl glucoside, lauryl glucoside) as well as polyglucosides (e.g. cellulose);
(9) Mono, di and trialkyl phosphates as well as mono, di and/or tri-PEG-alkylphosphates and salts thereof;
(10) Wool wax alcohols;
(11) Polysiloxane-polyalkyl-polyether copolymers or corresponding derivatives;
(12) Mixed esters of pentaerythritol, fatty acids, citric acid and fatty alcohol according to the Patent DE 1165574 and /or mixed esters of fatty acids with 6 to 22 carbon atoms, methyl glucose and polyols, preferably glycerin or polyglycerin,
(13) Polyalkylene glycols and
(14) Glycerin carbonate.

The addition products of ethylene oxide and/or propylene oxide on fatty alcohols, fatty acids, alkyl phenols, glycerin mono and diesters as well as sorbitol mono and diesters of fatty acids or on castor oil represent known, commercially available products. They can be considered as mixtures of homologs, whose mean degree of alkoxylation corresponds to the ratio of amounts of ethylene oxide and/or propylene oxide, used for the addition reaction, and that of the substrate. $C_{12/18}$ fatty acid mono and diesters of addition products of ethylene oxide on glycerin are known from DE 2024051 as greasing agents for cosmetic preparations.

Alkyl and/or alkenyl mono and oligoglycosides, their manufacture and use are known from the prior art. Their manufacture results particularly from the reaction of glucose or oligosaccharides with primary alcohols containing 8 to 18 carbon atoms. As far as the glycoside radicals are concerned, both monoglycosides, in which a cyclic sugar radical is glycosidically linked to the fatty alcohol, and also oligomeric glycosides, with a degree of oligomerization of preferably about 8, are suitable. In this context, the oligomerization degree is a statistical mean value based on the typical homolog distribution of such technical products.

Typical examples of suitable polyglycerin esters are polyglyceryl-2 dipolyhydroxystearate (Dehymuls® PGPH), polyglycerin-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate and mixtures thereof.

Moreover, zwitterionic surfactants can be used as emulsifiers. Zwitterionic surfactants are designated as those surface-active compounds that carry at least a quaternary ammonium group and at least a carboxylate and a sulfonate group in the molecule. Particularly suitable zwitterionic surfactants are the so-called betaines such as the N-alkyl-N,N-dimethylammonium glycinates, for example, the cocoalkyldimethylammonium glycinate, N-acylaminopropyl-N,N-dimethylammonium glycinates, for example, the cocoacylaminopropyldimethylammonium glycinate, and 2-alkyl-3-carboxymethyl-3-hydroxyethyl imidazolines with 8 to 18 carbon atoms in each of the alkyl or acyl groups, as well as cocoacylaminoethylhydroxyethylcarboxymethyl glycinate. The known fatty acid derivative known under the CTFA-description Cocamidopropyl Betaine is particularly preferred. Similarly, ampholytic surfactants are suitable emulsifiers. The ampholytic surfactants are understood to include such surface-active compounds that apart from a $C_{8/18}$ alkyl or acyl group, contain at least one free amino group and at least one COOH or $SO_3H$ group in the molecule, and are able to form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycine, N-alkyltaurines, N-alkylsarcosines, 2-alkylaminopropionic acids and alkylaminoacetic acids with about 8 to 18 C atoms in each alkyl group. Particularly preferred ampholytic surfactants are N-cocoalkylamino propionate, cocoacylaminoethylamino propionate and $C_{12/18}$-acyl sarcosine. Beside the ampholytics, the quaternary emulsifiers can also be considered, wherein the esterquats, preferably methyl quaternized difatty acid triethanolamine ester salts are particularly preferred.

As greasing agents, substances such as lanolin and lecithin, as well as polyethoxylated or acylated lanolin and lecithin derivatives, polyol fatty acid esters, monoglycerides and fatty acid alkanolamides can be used, the last ones serving as foam stabilizers at the same time.

Exemplary pearlizing waxes include: alkylene glycol esters, specifically ethylene glycol distearate; fatty acid alkanolamides, specifically cocofatty acid diethanolamide; partial glycerides, specifically monoglyceride of stearic acid; esters of polyfunctional, optionally hydroxy-substituted carboxylic acids with fatty alcohols with 6 to 22 carbon atoms, specifically long chain esters of tartaric acid; solids, such as, for example, fatty alcohols, fatty ketones, fatty aldehydes, fatty ethers and fatty carbonates, which have a total of at least 24 carbon atoms, specifically lauron and distearyl ether; fatty acids like stearic acid, hydroxystearic acid or behenic acid, ring opened products of olefin epoxides having 12 to 22 carbon atoms with fatty alcohols with 12 to 22 carbon atoms and/or polyols having 2 to 15 carbon atoms and 2 to 10 hydroxyl groups and mixtures thereof.

Consistence agents primarily include fatty alcohols or hydroxyfatty alcohols having 12 to 22 and preferably 16 to 18 carbon atoms, besides partial glycerides, fatty acids or hydroxyfatty acids. A combination of these materials with alkyl oligo glucosides and/or fatty acid N-methylglucamides of the same chain length and/or polyglycerin poly-12-hydroxystearates is preferred.

Suitable thickeners are for example, aerosil types (hydrophilic silicic acids), polysaccharides, especially xanthane gum, guar-guar, agar-agar, alginates and tyloses, carboxymethyl cellulose and hydroxyethyl cellulose, in addition, higher molecular polyethylene glycol mono- and-diesters of fatty acids, polyacrylates, (e.g. Carbopole® from Goodrich or Synthalene® from Sigma), polyacrylamides, polyvinyl alcohol and polyvinyl pyrrolidone, surfactants such as for example, ethoxylated fatty acid glycerides, esters of fatty acids with polyols such as pentaerythritol or trimethylolpropane, fatty alcohol ethoxylates with narrowed homolog distribution or alkyl oligo glucosides as well as electrolytes like cooking salt and ammonium chloride.

Exemplary suitable cationic polymers are cationic cellulose derivatives, such as e.g. a quaternized hydroxyethyl cellulose, available under the trade name Polymer JR 400® from Amerchol, cationic starches, copolymers of diallylammonium salts and acrylamides, quaternized vinyl pyrrolidone/vinyl imidazole polymers, such as e.g. Luviquat® (BASF), condensation products of polyglycols with amines, quaternized collagen polypeptides, such as for example, lauryldimonium hydroxypropyl hydrolyzed collagen (Lamequat®/Grünau), quaternized wheat polypeptides, polyethylene imine, cationic silicone polymers, such as for example, amidomethicone, copolymers of adipic acid and dimethylaminohydroxypropyldiethylene triamine (Cartaretine®/Sandoz), copolymers of acrylic acid and dimethyidiallylammonium chloride (Merquat® 550/Chemviron), polyaminopolyamides, such as e.g. described in FR 2252840 A as well as their crosslinked water-soluble polymers, cationic chitin derivatives such as e.g. quaternized chitosan, optionally microcrystallinically dispersed, condensation products of dihaloalkylenes, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from the Celanese Company, quaternized ammonium salt polymers, such as e.g. Mirapol® A-15, Mirapol® AD-1, Mirapol® AZ-1 from the Miranol Company.

Anionic, zwitterionic, amphoteric and nonionic polymers include, for example, vinyl acetate-crotonic acid copolymers, vinyl pyrrolidone-vinyl acrylate copolymers, vinyl acetate-butyl maleate-isobornyl acrylate copolymers, methyl vinyl ether-maleic anhydride copolymers and their esters, uncrosslinked polyacrylic acids and those crosslinked with polyols, acrylamidopropyltrimethylammonium chloride-acrylate copolymers, octylacylamide-methyl methacrylate-tert.-butylaminoethyl methacrylate-2-hydroxypropyl methacrylate copolymers, polyvinyl pyrrolidone, vinyl pyrrolidone-vinyl acetate copolymers, vinyl pyrrolidone-dimethylaminoethyl methacrylate-vinyl caprolactam terpolymers as well as optionally derivatized cellulose ethers and silicones.

Exemplary suitable silicone compounds are dimethylpolysiloxanes, methylphenylpolysiloxanes, cyclic siloxanes as well as amino-, fatty acid-, alcohol-, polyether-, epoxy-, fluorine-, glycoside- and/or alkyl modified silicone compounds, which may be both liquid or also resinous at room temperature. Simethicones, which are mixtures of dimethicones having an average chain length of 200 to 300 dimethylsiloxane units and hydrated silicates, are also suitable. A detailed review of suitable volatile silicones is found in Todd et al., Cosm. Toil. 91, 27, (1976).

Typical examples of fats are glycerides; waxes include inter alia natural waxes such as e.g. candelilla wax, carnauba wax, Japan wax, esparto grass wax, cork wax, guarum wax, rice oilseed wax, raw sugar wax, ouricury wax, montan wax, beeswax, shellac wax, spermaceti, lanolin (wool wax), fowl fat, ceresine, ozokerite (mineral wax), petrolatum, paraffin waxes microwaxes; chemically modified waxes (hard waxes), such as e.g. montan ester waxes, Sasol waxes, hydrogenated jojoba waxes as well as synthetic waxes, such as e.g. polyalkylene waxes and polyethylene glycol waxes.

Metal salts of fatty acids, such as e.g. magnesium-, aluminum- and/or zinc stearate or ricinoleate can be used as stabilizers.

Biogenetic active agents are understood to mean for example, tocopherol, tocopherol acetate, tocopherol palmitate, ascorbic acid, desoxyribonucleic acid, retinol, bisabolol, allantoin, phytanetriol, panthenol, AHA-acids, amino acids, ceramides, pseudoceramides, essential oils, plant extracts and vitamin complexes.

Cosmetic deodorants act against body odors, masking or eliminating them. Body odors result from the action of skin bacteria on apocrine sweat, whereby unpleasant smelling degradation products are formed. Accordingly, deodorants contain active principles, which act as germicides, enzyme inhibitors, odor absorbers or odor masks.

As germicides, which can be optionally added to the cosmetics according to the invention, basically all substances that are active against gram-positive bacteria are suitable, such as e.g. 4-hydroxybenzoic acid and its salts and esters, N-(4-chlorophenyl)-N'-(3,4-dichlorophenyl) urea, 2,4,4'-trichloro-240 -hydroxydiphenyl ether (Triclosan), 4-chloro-3,5-dimethylphenol, 2,2'-methylene-bis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propinylbutyl carbamate, chlorhexidine, 3,4,4'-trichlorocarbanilide (TTC), antibacterial fragrances, menthol, mint oil, phenoxyethanol, glycerin monolaurate (GML), diglycerin monocaprinate (DMC), salicylic acid-N-alkylamides such as, e.g. salicylic acid n-octylamide or salicylic acid n-decylamide.

Enzyme inhibitors can also be added to the inventive cosmetics. Examples of possible suitable enzyme inhibitors are esterase inhibitors. In this respect, trialkyl citrates are preferred, such as trimethyl citrate, tripropyl citrate, triisopropyl citrate, tributyl citrate and particularly triethyl citrate (Hydagen® CAT, Henkel KgaA, Dusseldorf/Germany). The substances inhibit the enzymatic activity and thereby reduce the odor formation. Additional substances that can be considered as esterase inhibitors are sterol sulfates or -phosphates, such as e.g. lanosterin-, cholesterin-, campesterin-, stigmasterin- and sitosterin sulfate or -phosphate, dicarboxylic acids and their esters, such as e.g. glutaric acid, monoethyl glutarate, diethyl glutarate, adipic acid, monoethyl adipate, diethyl adipate, malonic acid and diethyl malonate, hydroxycarboxylic acids and their esters such as e.g. citric acid, malic acid, tartaric acid or diethyl tartrate, as well as zinc glycinate.

Suitable odor absorbers are substances, which take up the odor forming compounds and firmly block them. They reduce the partial pressures of the individual components and thus also reduce their rate of propagation. It is important that the perfumes remain unaffected by this. Odor absorbers have no activity against bacteria. They comprise as the major component, for example, a complex zinc salt of ricinoleic acid or specific, largely odor-neutral fragrances, which are known to the person skilled in the art as fixing agents, such as e.g. extracts of labdanum or styrax or specific abietic acid derivatives. Fragrances or perfume oils act as masking agents and in addition to their function as masking agents, lend the deodorants their particular fragrance note. Exemplary perfume oils include mixtures of natural and synthetic aromas. Natural aromas are extracts of flowers, stalks and leaves, fruits, fruit skins, roots, branches, herbs and grasses, needles and twigs as well as resins and balsams. In addition, animal materials such as e.g. civet and castoreum can be considered. Typical synthetic aroma compounds are products of the type of the esters, ethers, aldehydes, ketones, alcohols and hydrocarbons.

Antiperspirants reduce sweat formation by influencing the activity of the ecrinal sweat glands and thereby act against armpit moisture and body odor. Aqueous or anhydrous formulations of antiperspirants typically contain the following ingredients:

(a) astringent principles,
(b) oil components
(c) nonionic emulsifiers,
(d) co emulsifiers,
(e) structurants,
(f) auxiliaries such as e.g. thickeners or complexing agents and/or
(g) non-aqueous solvents such as e.g. ethanol, propylene glycol and/or glycerin.

Salts of aluminum, zirconium or zinc are the main suitable astringent antiperspirant active principles. Such suitable antihydrotically active substances are e.g. aluminum chloride, hydrated aluminum chloride, hydrated aluminum dichloride, hydrated aluminum sesquichloride and their complexes e.g. with 1,2-propylene glycol, aluminum hydroxy allantoinate, aluminum chloride tartrate, aluminum-zirconium-trichlorohydrate, aluminum-zirconium-tetrachlorohydrate, aluminum-zirconium-pentachlorohydrate and their complex compounds e.g. with amino acids such as glycine.

The antiperspirants can also comprise standard oil-soluble and water-soluble auxiliaries in minor amounts. Such oil-soluble auxiliaries can be, for example:

anti-inflammatory, skin-protecting or fragrant ethereal oils,
synthetic skin-protecting active principles and/or
oil-soluble perfume oils.

Typical water-soluble additives are e.g. preservatives, water-soluble fragrances, pH adjustors, e.g. buffer mixtures, water-soluble thickeners, e.g. water-soluble natural or synthetic polymers such as e.g. xanthane gum, hydroxyethyl cellulose, polyvinyl pyrrolidone or high-molecular polyethylene oxides.

Climbazole, octopirox and zinc pyrethion can be used as anti-dandruff agents.

Usable film builders are for example, chitosan, microcrystalline chitosan, quaternized chitosan, polyvinyl pyrrolidone, vinyl pyrrolidone-vinyl acetate copolymers, polymers of the acrylic acid series, quaternized cellulose derivatives, collagen, hyaluronic acid or its salts and similar compounds.

As swelling agents for the aqueous phase, montmorillonite, mineral clays, Pemulen® as well as Carbopol types (Goodrich) can be used. Further suitable polymers or swelling agents can be found in the review by R. Lochhead in Cosm. Toil. 108, 95 (1993).

The UV-light protective factors are understood for example, to be organic substances (protective light filters) that are liquid or solid at room temperature and which are able to absorb UV-radiation and emit the resulting energy in the form of longer wavelength radiation, for example, as heat. UVB filters can be oil-soluble or water-soluble. As oil-soluble substances, the following may be cited:

3-Benzylidenecamphor or 3-benzylidenenorcamphor and its derivatives, e.g. 3-(4-methylbenzylidene)camphor as described in EP 0693471 B1;

4-Aminobenzoic acid derivatives, preferably 2-ethylhexyl 4-dimethylamino)benzoate, 2-octyl 4-(dimethylamino) benzoate and amyl 4-(dimethylamino)benzoate;

Esters of cinnamic acid, preferably 2-ethylhexyl 4-methoxycinnamate, propyl 4-methoxycinnamate, isoamyl 4-methoxycinnamate, 2-ethylhexyl 2-Cyano-3,3-phenylcinnamate (Octocrylene);

Esters of salicylic acid, preferably 2-ethylhexyl salicylate, 4-isopropylbenzyl salicylate, homomenthyl salicylate;

Derivatives of benzophenone, preferably 2-hydroxy-4-methoxybenzophenone, 2-hydroxy-4-methoxy-4'-methylbenzophenone, 2,2'-dihydroxy-4-methoxybenzophenone;

Esters of benzalmalonic acid, preferably di-2-ethylhexyl 4-methoxybenzmalonate;

Triazine derivatives, such as e.g. 2,4,6-trianilino-(p-carbo-2'-ethyl-1'-hexyloxy)-1,3,5-triazine and octyl triazone, as described in EP 0818450 A1 or dioctyl butamido triazone (Uvasorb® HEB);

Propane-1,3-dione, such as e.g. 1-(4-tert.butylphenyl)-3-(4'-methoxyphenyl)propane-1,3-dione;

Ketotricyclo(5.2.1.0)decane derivatives, as described in EP 0694521 B1.

Water-soluble substances include:

2-Phenylbenzimidazole-5-sulfonic acid and its alkaline-, alkaline earth-, ammonium-, alkylammonium-, alkanolammonium- and glucammonium salts;

Sulfonic acid derivatives of benzophenones, preferably 2-hydroxy-4-methoxybenzophenone-5-sulfonic acid and its salts;

Sulfonic acid derivatives of 3-benzylidenecamphor, such as e.g. 4-(2-oxo-3-bornylidenemethyl)benzene sulfonic acid and 2-methyl-5-(2-oxo-3-bornylidene)sulfonic acid and its salts.

Typical UV-A filters particularly include derivatives of benzoylmethane, such as, for example, 1-(4'-tert.-butylphenyl)-3-(4'-methoxyphenyl)propane-1,3-dione, 4-tert.-butyl-4'-methoxydibenzoylmethane (Parsol 1789), 1-phenyl-3-(4'-isopropylphenyl)-propane-1,3-dione as well as enamine compounds, as described in DE 19712033 A1 (BASF). Naturally, the UV-A and UV-B filters can also be added as mixtures. Beside the cited soluble materials, insoluble, light protective pigments, namely finely dispersed, metal oxides or salts can also be considered for this task. Exemplary suitable metal oxides are particularly zinc oxide and titanium oxide and also oxides of iron, zirconium, silicon, manganese, aluminum and cerium as well as their mixtures. Silicates (talc), barium sulfate or zinc stearate can be added as salts. The oxides and salts are already used in the form of pigments for skin care and skin protecting emulsions and decorative cosmetics. Here, the particles should have a mean diameter of less than 100 nm, preferably between 5 and 50 nm and especially between 15 and 30 nm. They can be spherical, however elliptical or other shaped particles can also be used. The pigments can also be surface treated, i.e. hydrophilized or hydrophobized. Typical examples are coated titanium dioxides, such as, for example, Titandioxid T 805 (Degussa) or Eusolex® T2000 (Merck). Hydrophobic coating agents preferably include trialkoxy octylsilanes or Simethicones. Sunprotection agents preferably contain micropigments or nanopigments. Micronized zinc oxide is preferably used. Further suitable UV light protection filters may be found in the review by P. Finkel in SöFW-Journal, Volume 122 (1996), p. 543.

As well as both above-cited groups of primary light protective materials, secondary light protective agents of the antioxidant type can also be used, which interrupt photochemical chain reactions that are propagated when the UV-radiation penetrates the skin. Typical examples are amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotinoides, carotines (e.g. α-carotine, β-carotine, lycopine) and their derivatives, chlorogenic acid and their derivatives, liponic acid and their derivatives e.g. dihydroliponic acid), aurothioglucose, propylthiouracil and other thiols e.g. thioredoxine, glutathione, cystein, cystine, cystamine and their glycosyl-, n-acetyl-, methyl-, ethyl-, propyl-, amyl-, butyl- and lauryl-, palmitoyl-, oleyl-, ?-linoleyl-, cholesteryl- and glyceryl esters) as well as their salts, dilauryl thiodipropionate, distearyl thiodipropionate, thiodipropionic acid and their derivatives (esters, ethers, peptides, lipids, nucleotides, nucleosides and salts) as well as sulfoximine compounds (e.g. buthioninesulfoximines, homocysteinsulfoximine, butionine sulfone, penta-, hexa-, heptathionine sulfoximine) in very minor compatible doses e.g. pmol to μmol/kg), further (metal)-chelates (e.g. α-hydroxyfatty acids, palmitic acid, phytinic acid, lactoferrin), α-hydroxyacids (e.g. citric acid, lactic acid, malic acid), humic acid, gallic acid, gall extracts, bilirubin, biliverdin, EDTA, EGTA and their derivatives, unsaturated fatty acids and their derivatives e.g. ?-linolenic acid, linoleic acid, oleic acid), folic acid and their derivatives, ubiquinone and ubiquinol and their derivatives, vitamin C and derivatives (e.g. ascorbyl palmitate, Mg-ascorbyl phosphate, ascorbyl acetate), tocopherols and derivatives (e.g. vitamin-E-acetate), vitamin A and derivatives vitamin-A-palmitate) as well as coniferyl benzoate of benzoic resin, rutinic acid and their derivatives, α-glycosylrutine, ferula acid, furfurylidenegluci-tol, carnosine, butylhydroxytoluene, butylhydroxyanisol, nordihydroguajac resin acid, nordihydroguajaret acid, trihydroxybutyrophenone, uric acid and their derivatives, mannoses and their derivatives, superoxide-dismutase, zinc and its derivatives e.g. $ZnO$, $ZnSO_4$) selenium and its derivatives (e.g. selenium-methionine), stilbenes and their derivatives (e.g. stilbene oxide, trans-stilbene oxide) and the inventively suitable derivatives (salts, esters, ethers, sugars, nucleotides, nucleosides, peptides and lipids) of these cited active substances.

To improve the flow properties, hydrotropes can also be added, such as, for example, ethanol, isopropyl alcohol, or polyols. Polyols, which are considered, possess preferably 2 to 15 carbon atoms and at least two hydroxyl groups. The polyols can comprise further functional groups, especially amino groups, or can be modified by nitrogen. Typical examples are glycerin;

alkylene glycols, such as, for example, ethylene glycol, diethylene glycol, propylene glycol, butylene glycol, hexylene glycol as well as polyethylene glycols with an average molecular weight of 100 to 1000 daltons;

industrial oligoglycerin mixtures with a degree of self condensation of 1.5 to 10 like for instance industrial diglycerin mixtures with a diglycerin content of 40 to 50 wt. %;

methylol compounds like in particular, trimethylol ethane, trimethylol propane, trimethylol butane, pentaerythreitol and dipentaerythritol;

lower alkyl glucosides, particularly those with 1 to 8 carbon atoms in the alkyl group, such as, for example, methyl and butyl glucoside;

sugar alcohols with 5 to 12 carbon atoms, such as, for example, sorbitol or mannitol, sugars with 5 to 12 carbon atoms, such as, for example, glucose or saccharose;

amino sugars, such as for example, glucamine;

dialcoholamines, such as diethanolamine or 2-amino-1,3-propanediol.

Suitable preservatives are, for example, phenoxyethanol, formaldehyde solution, parabene, pentanediol or sorbic acid as well as the further classes of materials described in Appendix 6, part A and B of the Cosmetics Regulation. Insect repellants include N,N-diethyl-m-toluamide, 1,2-pentanediol, or ethyl butylacetylamino propionate; suitable self-tanning agents include dihydroxyacetone.

As perfume oils, the known mixtures of natural and synthetic aromas can be cited. Natural aromas are extracts of flowers (lilies, lavender, roses, jasmine, neroli, ylang ylang), stalks and leaves (geranium, patchouli, petit grain), fruits (aniseed, coriander, caraway, juniper), fruit skins (bergamot, lemons, oranges), roots (mace, angelica, celery, cardamom, costic, iris, calmus), wood (pine, sandal, guava, cedar, rose wood), herbs and grasses (tarragon, lemon grass, sage, thyme), needles and twigs (spruce, fir, scotch pine, larch), resins and balsam (galbanum, elemi, benzoin, myrrh, olibanum, opoponax). In addition, animal materials such as e.g. civet and castoreum can be considered. Typical synthetic aroma compounds are products of the type of the esters, ethers, aldehydes, ketones, alcohols and hydrocarbons.

As colorants, those substances suitable and approved for cosmetic purposes can be used, as summarized, for example, in the publication "Kosmetische Färbemittel" of the Colorant Commission of the Deutsche Forschungsgemeinschaft, Verlag Chemie, Weinheim, 1984, p. 81-106. These colorants are typically used in concentrations of 0.001 to 0.1 wt. %, based on the total mixture.

The total content of auxiliaries and additives can be 1 to 50, preferably 5 to 40 wt. %, based on the composition. The composition can be manufactured using customary cold or hot processes; preferably according to the phase inversion temperature method.

The inventive mouth, tooth and/or dental prostheses care agents can exist, for example, as gels, liquid toothpaste, viscous toothpaste, denture cleaners or adhesive creams for prostheses.

For this it is necessary to mix the inventive compounds into a suitable carrier.

Suitable carriers can also be e.g. powdered preparations or aqueous-alcoholic solutions that comprise 0 to 15 wt. % ethanol, 1 to 1.5 wt. % aromatic oils and 0.01 to 0.5 wt. % sweeteners as the mouth wash or 15 to 60 wt. % ethanol, 0.05 to 5 wt. % aromatic oils, 0.1 to 3 wt. % sweeteners and optional additional auxiliaries as the mouth wash concentrate that is diluted with water before use. Accordingly, the concentration of the components must be chosen at a high enough level such that during the application after dilution they do not fall below the cited lower concentration limits.

However, gels and more or less flowable pastes can also serve as carriers and which can be pressed out of flexible plastic containers or tubes and applied to the teeth by means of a toothbrush. Such products comprise higher quantities of moisturizers and binders or consistency regulators and polishing components. Moreover, these preparations also comprise aromatic oils, sweeteners and water.

For example, glycerin, sorbitol, xylitol, propylene glycols, polyethylene glycols or mixtures of these polyols, in particular, those polyethylene glycols with molecular weights from 200 to 800 (from 400-2000) can be comprised and used as moisturizers. The preferred moisturizer is sorbitol, comprised in an amount of 25-40 wt. %.

Condensed phosphates in the form of their alkali salts, preferably in the form of their sodium or potassium salts, can be included as anti-tartar active substances and as demineralization inhibitors. Due to the hydrolytic effect, the aqueous solutions of these phosphates are alkaline. The pH of the inventive mouth-, tooth- and/or dental prostheses care agents is adjusted to the preferred value of 7.5-9 by the addition of acid. Mixtures of various condensed phosphates or also hydrated salts of condensed phosphates can also be added. The specified quantities of 2-12 wt. % refer, however, to the anhydrous salts. A sodium or potassium tripolyphosphate in a concentration of 5 to 10 wt. % is preferred as the condensed phosphate.

A preferred comprised active substance is a caries-inhibiting fluorine compound, preferably from the group of fluorides or monofluorophosphates, in an amount of 0.1 to 0.5 wt. % fluorine. Suitable fluorine compounds are e.g. sodium monofluorophosphate ($Na_2PO_3F$), potassium monofluorophosphate, sodium or potassium fluoride, tin fluoride or the fluoride of an organic amino-compound.

Natural and synthetic water-soluble polymers, such as carrageen, traganth, guar, starch and their non-ionic derivatives such as e.g. hydroxypropyl guar, hydroxyethyl starch, cellulose ethers such as e.g. hydroxyethyl cellulose or methylhydroxypropyl cellulose serve as exemplary binding agents and consistence regulators. Also agar-agar, xanthane gum, pectins, water-soluble carboxyvinyl polymers (e.g. Carbopol® types) polyvinyl alcohol, polyvinyl pyrrolidone, higher molecular polyethylene glycols (molecular weight $10^3$ to $10^6$ D). Additional substances that are suitable for controlling viscosity are layered silicates such as e.g. montmorillonite clays, colloidal thickening silicas, e.g. aerogel silica or pyrogenic silicas.

As preferred polishing components are added all the polishing agents known for this, but preferably precipitated and gelled silicas, aluminum hydroxide, aluminum silicate, aluminum oxide, aluminum oxide trihydrate, insoluble sodium metaphosphate, calcium pyrophosphate, calcium hydrogen phosphate, dicalcium phosphate, chalk, hydroxyapatite, hydrotalcite, talcum, magnesium aluminum silicate (Veegum®), calcium sulfate, magnesium carbonate, magnesium oxide, sodium aluminum silicate, e.g. zeolite A or organic polymers e.g. polymethyl acrylate. The polishing agents are advantageously used in smaller amounts of e.g. 1 to 10 wt. %.

The organoleptic properties of the inventive tooth- and/or mouth care products can be improved by the addition of aromatic oils and sweeteners. All the natural and synthetic aromas suited for mouth-, tooth- and/or tooth prostheses can be considered as the aromatic oils. Natural aromas can be used both in the form of ethereal oils isolated from drugs and also from individual components isolated from them. Preferably at least one aromatic oil is comprised from the group peppermint oil, spearmint oil, anisole, caraway oil, eucalyptus oil, fennel oil, cinnamon oil, geranium oil, sage oil, oil of thyme, markoram oil, oil of basil, lemon oil, gaultheria oil or one or a plurality of the synthetically produced isolated components of these oils. The most important components of the cited oils are e.g. menthol, carvone, anethol, cineol, eugenol, cinnamaidehyde, geraniol, citronellol, linalool, salven, thymol, terpenes, terpineol, methyl chavicol and methyl salicylate. Further suitable aromas are e.g. menthyl acetate, vanillin, ionone, linalyl acetate, rhodinol and piperitone. Either natural sugars, such as sucrose, maltose, lactose and fructose, or synthetic sweeteners such as e.g. saccharin, sodium salt, sodium cyclamate or aspartam are suitable edulcorants.

In particular, alkyl and/or alkenyl-(oligo)glycosides can be used as the surfactants. Their manufacture and use as surface active materials are known, for example, from U.S. Pat. No. 3,839,318, U.S. Pat. No. 3,707,535, U.S. Pat. No. 3,547,828, DE-A-19 43 689, DE-A-20 36 472 and DE-A-30 01 064 as well as EP-A-77 167. As far as the glycoside groups are concerned, both monoglycosides (x=1), in which a pentose or hexose group is glycosidically linked to a primary alcohol having 4 to 16 carbon atoms, and also oligomeric glycosides, with a degree of oligomerization x up to 10, are suitable. In this context, the oligomerization degree is a statistical mean value based on the typical homolog distribution of such technical products.

Preferred suitable alkyl and/or alkenyl-(oligo) glycosides are an alkyl and/or alkenyl-(oligo) glucoside of the Formula $RO(C_6H_{10}O)_x$—H, in which R is an alkyl and/or an alkenyl group with 8 to 14 carbon atoms and x has a mean value from 1 to 4. Alkyl oligo glucosides based on hydrogenated $C_{12/14}$-coco alcohol with a DP of 1 to 3 are particularly preferred. The alkyl and/or alkenyl glycoside surfactant can be used very sparingly, amounts of 0.005 to 1 wt. % being already sufficient.

Apart from the cited alkylglucoside surfactants, other non-ionic, ampholytic and cationic surfactants can also be comprised, examples being: fatty alcohol polyglycol ether sulfonates, monoglyceride sulfates, monoglyceride ether sulfates, mono and/or dialkyl sulfosuccinates, fatty acid isethionates, fatty acid sarcosinates, fatty acid taurides, fatty acid glutamates, ether carboxylic acids, fatty acid glucamides, alkylamidobetaines and/or protein-fatty acid condensates, the last preferably on the basis of wheat proteins. A non-ionic solubilizer from the group of the surface-active compounds can be required, particularly for solubilizing the mostly water-insoluble aromatic oils. For example, oxethylated fatty acid glycerides, oxethylated fatty acid sorbitol partial esters or fatty acid partial esters of glycerin-oxethylates or sorbitol-oxethylates are suitable for this task. Solubilizers from the group of the oxethylated fatty acid glycerides primarily include addition products of 20 to 60 moles ethylene oxide on mono and diglycerides of linear fatty acids having 12 to 18 carbon atoms or on triglycerides of hydroxy-fatty acids such as oxystearic acid or ricinoleic acid. Further suitable solubilizers are oxethylated fatty acid sorbitol partial esters; they are preferably addition products of 20 to 60 moles ethylene oxide on monoesters of sorbitol and diesters of sorbitol with fatty acids having 12 to 18 carbon atoms. Equally suitable solubilizers are fatty acid partial esters of glycerin oxethylates or sorbitol oxyethylates; they are preferably monoesters and diesters of $C_{12}$-$C_{18}$-fatty acids and addition products of 20 to 60 moles ethylene oxide on 1 mole glycerin or on 1 mole sorbitol.

The inventive mouth, tooth and/or dental prostheses care agents preferably comprise addition products of 20 to 60 moles ethylene oxide on hydrogenated or non-hydrogenated castor oil (i.e. on oxystearic acid triglyceride or ricinoleic acid triglyceride), on glycerin mono and/or distearate or on sorbitol mono and/or distearate, as the solubilizer for the optionally comprised aromatic oils.

Additional typical additives for the mouth, tooth and/or dental prostheses care agents are e.g.

Pigments, e.g. titanium dioxide, and/or colorants pH adjustors and buffer substances such as e.g. sodium bicarbonate, sodium citrate, sodium benzoate, citric acid, phosphoric acid or acidic salts, e.g. $NaH_2PO_4$ Wound healing and anti-inflammatory substances such as e.g. allantoin, urea, panthenol, azulene or camomile extract Further active materials against tartar such as e.g. organo-phosphonates, e.g. hydroxyethane diphosphonates or azacycloheptane diphosphonate Preservatives such as e.g. salts of sorbic acid, esters of p-hydroxybenzoic acid.

Plaque-inhibitors such as e.g. hexachlorophene, chlorhexidine, hexetidine, triclosan, bromochlorophene, phenyl salicylate.

In a particular embodiment, the composition is a mouthwash, a mouth water, a denture cleaner or a denture adhesive.

For inventively preferred denture cleaners, particularly denture cleaning tablets and powder, besides the ingredients already mentioned for mouth, tooth and/or dental prostheses care, peroxy compounds such as for example, peroxyborate, peroxymonosulfate or percarbonate are also suitable. They have the advantage that besides the bleaching activity, they simultaneously act as deodorizers and/or as disinfectants. Such peroxy compounds are added in denture cleaners in the range between 0.01 and 10 wt. %, particularly between 0.5 and 5 wt. %.

Enzymes, such as proteases and carbohydrases are also suitable as additional ingredients for decomposing proteins and carbohydrates. The pH can be between pH 4 and pH 12, in particular, between pH 5 and pH 11.

In addition, further auxiliaries are required for the denture cleaning tablets, such as for example, agents that initiate an effervescence, such as e.g. $CO_2$-releasing materials such as sodium hydrogen carbonate, fillers, e.g. sodium sulfate or dextrose, lubricants, e.g. magnesium stearate, flow regulators, such as for example, colloidal silicon dioxide and granulating agents, such as the already cited high molecular weight polyethylene glycols or polyvinyl pyrrolidone.

Denture adhesives can be offered as powders, creams, films or liquids and support the adhesion of the dentures. Natural and synthetic swelling agents are suitable as active principles. Besides alginates, vegetal gums, such as e.g. gum arabicum, traganth and karayi gum as well as natural rubber are to be understood as natural swelling agents. In particular, alginates and synthetic swelling agents, such as e.g. sodium carboxymethyl cellulose, high molecular weight ethylene oxide copolymers, salts of polyvinyl ether-maleic acid and poly-acrylamides are suitable.

In particular, hydrophobic.foundations, especially hydrocarbons, such as for example, white vaseline (DAB) or paraffin oil, are especially suitable as the auxiliaries for pasty and liquid products.

The inventive compounds are suitable for inhibiting microbial growth, wherever this growth is not wanted, e.g. in aqueous systems in numerous industrial applications, such as paper manufacturing. A number of important industries are strongly affected by the activity of these bacteria, algae and fungi on the raw materials used, on various aspects of their manufacturing activities or on the manufactured end products. These industries include colorant, wood, textile, cosmetic, leather, tobacco, hide, rope, paper, pulp, plastic, fuel, oil, rubber and machine industries. The important applications of the inventive compounds include: inhibition of the growth of bacteria and fungi in aqueous colorants, adhesives, latex emulsions and grouting compounds; wood conservation; cutting oil conservation; combating mucus-producing bacteria and fungi in pulp and paper mills and cooling water; as spray or dipping treatments for textiles and leather to prevent mold growth; as components in anti-fouling paints to prevent adhesion of fouling organisms; protection of coating films, particularly exterior colors, against the attack of fungi, which occurs on weathering of the coating film; protection of processing equipment from slime deposits during the manufacture of cane sugar and sugar beet; prevention of enrichment and deposition of microorganisms in washing exhaust systems and in industrial fresh water supply systems; combating contamination and deposition of microorganisms in and with cutting oil liquids and cutting oil slurries as well as in secondary crude oil refining processes; inhibition of bacterial and fungal growth in paper coating processes, which could influence the quality of the paper coating; combating bacterial and fungal growth and their deposition in the manufacture of various special cardboards, e.g. cardboard and particle boards; prevention of the discoloration of the cell sap of freshly cut wood of various types; combating bacterial and fungal growth in clay and pigment slurries of various kinds that are manufactured for later use, for example, for paper coating and color manufacture, and which are subject to degradation from microorganisms during storage and transport; as disinfectants for hard surfaces to prevent the growth of bacteria and fungi on walls, floors etc. as well as in swimming pools to protect against the growth of algae.

Combating bacteria and fungi is especially important in water systems of pulp and paper mills, which comprise aqueous dispersions of fibers for paper manufacture. The uncontrolled enrichment of slime from the accumulation of bacteria and fungi leads to qualitatively inferior production, lower production due to pauses and more frequent cleaning, increased consumption of raw materials as well as higher maintenance costs. The problem of slime deposition in the paper industry is aggravated by the wide use of closed white water systems.

A further important field, in which the combat against bacterial and fungal growth is decisive, are the clay and pigment slurries. These slurries consist of various clays, e.g. kaolin, and pigments, e.g. calcium carbonate and titanium dioxide. They are usually manufactured at one site that is a long way away from the final end-use, e.g. in paper coating and colorant manufacture, and are stored until subsequently transported to the end-user factory. The high quality standards for the paper and colorant end products, in which the slurry is used, require that the clay and pigment slurry has a very low microorganism content, in order for it to be utilizable for paper coating or colorant manufacture.

A further important area for combating microbial growth are cooling systems such as those with circulation cooling towers. These systems expose a large quantity of water to the atmosphere for a considerable time under conditions that include insufficient aeration and insufficient exposure to sunlight that would combat microbial growth, particularly bacterial and fungal growth. Moreover, many cooling towers dispose of a filling of beads of synthetic polymers or other materials in order to increase the heat exchange surface. This type of construction exacerbates the problem of microbial growth, as it provides the ideal physical environment for the proliferation of worrisome microbes. Uncombatted, these microorganisms flourish and produce colonies that are able to block the heat exchange surfaces with a biofilm and clog up the components of the water transport equipment used to run the cooling system. The inventive compounds provide an excellent combat against microbial growth in these systems.

The inventive compounds are particularly suited to combat the destructive action of microorganisms in water or aqueous media. Systems that use circulating water or circulating aqueous media are infected with microorganisms and their efficiency is considerably affected when microorganism deposits increase in the system. Deposits classified as slimes coat the walls of containers and other recipients, every machine and process equipment in use and cause blockages in pipes and valves. The presence of slime promotes corrosion of metal surfaces and facilitates the rot of wooden towers. The slimes also produce discolorations and other defects in all manufactured products and necessitate cost-intensive stoppage times. Combating microorganisms in aqueous media is particularly important when dispersed particles or fines are present, e.g. dispersed cellulose fibers and dispersed fillers and pigments in paper production as well as dispersed pigments in colorant production.

The inventive compounds can be added in pure form or as active constituents of mixtures, for example, as constituents of sterilization agents, disinfectants, impregnation agents or preservatives.

In the majority of cases, mixtures suitable for practical application comprise a total of 0 to 99, preferably 90 to 10 wt. % of additional conventional ingredients that are selected according to the defined application form and application.

For liquid preparations, for example, water-miscible organic solvents can be considered as solvents, for example, ethanol, isopropanol and ethylene glycol, propylene glycol, ethyl ethylene glycol, propyl propylene glycol 20 together with water-immiscible solvents such as, for example, white spirit, benzene, toluene, ethyl acetate or dimethylene chloride.

If in addition to the germ inhibiting action, an additional cleansing action is desired, then the inventive mixtures can also comprise surfactants, particularly non-ionic surfactants. Examples of suitable surfactants are $C_8$-$C_{18}$-alkylglucosides with about 1 to 10 glucose units in the molecule, addition products of 4 to 40, preferably 4 to 20 moles ethylene oxide on a mole of fatty alcohol, alkylcyclohexanol, alkylphenol, fatty acid, fatty acid amide or alkane sulfonamide. Addition products of 5 to 16 moles ethylene oxide on coco- or tallow fat alcohols, on oleyl alcohol, a mixture of oleyl alcohol and cetyl alcohol, as well as on mono, di or trialkylphenols and on monoalkylcyclohexanols with 6 to 14 carbon atoms in the alkyl group are of particular interest.

Mixed addition products of ethylene oxide and propylene oxide on the cited compounds having an active hydrogen atom also come into consideration.

The cited alkoxylation products can also be end capped, for example, with ether or acetal groups.

Additional builders can also be present in the inventive mixtures; for example, alkali salts of gluconic acid, particularly sodium gluconate, the alkali salts of nitrilotriacetic acid, ethylenediamine tetraacetic acid, hydroxyethanediphosphonic acid, phosphonobutanetricarboxylic acid, lactic acid, citric acid or tartaric acid. In addition, the water-soluble salts of higher molecular weight polycarboxylic acids also come into consideration as builders, for example, polymers of maleic acid, itaconic acid, fumaric acid and citraconic acid. Mixed polymers of these acids with one another or with other polymerisable monomers such as ethylene, propylene, acrylic acid, vinyl acetate, isobutylene, acrylamide and styrene can also be used. Cleaning boosters, such as fatty acid mono and diethanolamides, for example, the monoethanolamide and the diethanolamide of coco fatty acid, and addition products of up to 4 moles ethylene oxide or propylene oxide on fatty alcohols having 8 to 12 carbon atoms as well as free fatty alcohols having 8 to 12 carbon atoms, as well as cleaning boosters based on cellulose can also be blended into the inventive mixtures.

Moreover, it can be advantageous for further application areas if the agents comprise additional antimicrobially active substances. Insecticides such as e.g. pyrethroids (Permethrin, Cypermethrin, Decamethrin and Fenvalerate) and/or Lindane, Endosulfan, Dieldrin can also be blended into the inventive agents.

In general, the amounts of the possible constituents used for formulating the inventive agents are a function of commercial and price targets and in principle have no inventive significance.

For the manufacture of ready for use preservatives, besides liquid concentrates, solid products can also be provided, preferably in powder or granular form, which comprise the inventive compounds according to Formula I.

The inventive disinfectants and preservatives can be used in many situations, for example, in households and in industry such as hospitals, schools, bathing centers, public transport, industrial companies and factories.

Further, the inventive compounds can be used for conserving industrial products that will be subsequently processed such as inks, dispersion and emulsion paints, adhesives and glues, drilling and cutting oils or products for the paper, cardboard or leather working industries as well as for the conservation of industrial and waste water.

The application can be realized for example, by spraying, brushing, painting, coating, dipping or pressure- or vacuum impregnation.

The compounds according to Formula I are preferably added in a concentration in the range of 1 ppm to 1000 ppm, particularly 20 to 500 ppm, particularly preferably 20 to 100 ppm, especially 20 to 50 ppm.

The following examples illustrate the invention without, however, restricting it in any way.

EXAMPLES (a) Synthesis of Alkyloxylactones.

Example 1

Synthesis of a-Octyloxy-γ-butyrolactone

Starting Materials.

| 5.10 g | α-hydroxy-γ-butyrolactone | 50 mmol |
| 9.66 g | 1-bromooctane | 50 mmol |
| 16.29 g | cesium carbonate | 50 mmol |
| 80 ml | dimethylformamide (DMF) | |

Experimental.

50 mmol α-hydroxy-γ-butyrolactone is provided in absolute dimethylformamide. 50 mmol of cesium carbonate are added to this solution and 50 mmol of bromooctane (dissolved in absolute dimethylformamide) were added drop by drop within 5 minutes. The reaction mixture is held at T=70° C. for 76 hours, then cooled and filtered. The reaction is monitored by means of thin layer chromatography and GLC. After removal of the solvent there remains a red-brown residue that can be fractionally distilled.

Yield 20.6 g (85%) of a clear liquid, b. pt. 156-161° C. (0.08 mbar).

Example 2

Synthesis of a-Octyloxy-D-(−)-pantolactone

Starting Materials.

| 13.0 g | Pantolactone | 100 mmol |
| 19.3 g | 1-Bromooctane | 100 mmol |
| 32.6 g | cesium carbonate | 100 mmol |
| 200 ml | dimethylformamide (DMF) | |

Experimental.

100 mmol D-(−)-pantolactone are provided in absolute dimethylformamide. 100 mmol of cesium carbonate are added to this solution and 100 mmol of bromooctane (dissolved in absolute dimethylformamide) were added drop by drop within 5 minutes. The reaction mixture is held at room temperature for 48 hours, then cooled and swirled round. The reaction is monitored by means of thin layer chromatography and GLC. After removal of the solvent there remains a clear liquid that can be fractionally distilled under high vacuum.

Yield 5.06 g (48%) of a clear liquid, b. pt. 127-150° C. (0.06 mbar).

Example 3

Synthesis of (R)-a-Octyloxy-γ-Butyrolactone

Starting Materials.

| 2.00 g | R-(+)-α-hydroxy-γ-butyrolactone | 19 mmol |
| 3.67 g | 1-bromooctane | 19 mmol |
| 6.25 g | cesium carbonate | 19 mmol |
| 130 ml | dimethylformamide (DMF) | |

Experimental.

19 mmol R-(+)-α-Hydroxy-γ-butyrolactone are provided in absolute dimethylformamide. 19 mmol of cesium carbonate are added to this solution and 19 mmol of bromooctane (dissolved in absolute dimethylformamide) were added drop by drop within 5 minutes. The reaction is monitored by means of GLC. The reaction mixture is held at T=50° C. for 91 hours. After the reaction ends, the reaction mixture is cooled and filtered. After removal of the solvent the crude product is purified by means of flash column chromatography.

Yield 2.34 g (58%), light yellow clear liquid

Example 4

Synthesis of a-hexadecyloxy-γ-butyrolactone

Starting Materials.

| 5.10 g | α-hydroxy-γ-butyrolactone | 50 mmol |
| 15.74 g | 1-bromohexadecane | 50 mmol |
| 16.46 g | cesium carbonate | 50 mmol |
| 80 ml | dimethylformamide (DMF) | |

Experimental.

50 mmol α-hydroxy-γ-butyrolactone are provided in absolute dimethylformamide. 50 mmol of cesium carbonate are added to this solution and 50 mmol of 1-bromohexadecane (dissolved in absolute dimethylformamide) were added drop by drop within 5 minutes. The reaction mixture is held at T=70° C. for approximately 119 hours and the reaction is monitored by means of GLC. After the reaction ends, the reaction mixture is cooled and filtered. After removal of the solvent the crude product is purified by means of flash column chromatography.

Yield 5.53 g (34%) of a white solid material (b) Use of Alkyloxylactones for the Reduction of Biofilms on Glass Surfaces.

Experimental.

The germ *Pseudomonas aeruginosa* ATCC 15442 is cultivated at 37° C. on Caso-Agar overnight. A CFU (Colony Forming Unit) of solid medium is incubated in 50 ml Caso-broth at 37° C. for 7 hours and 150 rpm (1. passage). 100 μl germs from the washed liquid culture are carried over into 50 ml fresh Caso-nutrient medium and incubated at 37° C. for approximately 16 hours and 150 rpm. (2. Passage). A germ count of 106 CFU/ml is used from this second passage in the biofilm test. For the biofilm test, the germs in the above-mentioned concentration, together with a diluted complete medium (20 times with DGHM-water diluted TBY), are pipetted into a micro-titration plate (6-position chamber), which is used as the miniaturized biofilm test system. The active substances under test are added in the desired concentration to the mixture (3 ml). As controls, first, attempts were made with active substances, but without germs, as the active substances could already have an inherent color (negative control); secondly, diluted complete medium with germs, but without the active substances were also used as controls. In addition, 1 sterile glass plate (microscope slide), size 18×18, on the surface of which the biofilm growth is investigated, is placed into each of the 6-position chambers. For each starting material, triple determinations are carried out, i.e. three glass slides are investigated per starting material. The 6-position plates are shaken for 6 or 24 hours at 30° C. and 60 rpm. After the predetermined incubation times, 1 ml per starting material are removed for germ count determination, diluted in trypton-NaCl solution and plated out on Caso-Agar. The resulting plates are incubated for 24 hours at 37° C. and then counted. The slide glasses are taken out of the 6-positions to be dried at room temperature and then dyed in new 6-positions with 3 ml 0.01% SafraninO-solution (made up in sterile water) for 15 minutes. The colorant solution is then siphoned off, non-bound colorant is removed with water from the slide glasses and the colored slide glasses dried. The colored and dried surfaces of the slide glasses are scanned and evaluated using Corel Draw paint 9. In order to be able to subtract the background value (of the glass) from the measured value, additional untreated slide glasses are also scanned.

Results:

The results are presented in FIG. 1. In the first range finding experiments (three experiments independent from one another), noticeable differences in the biofilm formation were observed after 6 hours incubation with respect to the control without added active substance (set to 100% in FIG. 1) in comparison with the tests with the alkyloxylactones. 50 ppm and 100 ppm of each active substance were added to the starting materials. The test with 100 ppm octyloxybutyrolactone (H128) showed a biofilm reduction of approximately 40% (relative to the control); on increasing the concentration of active substance, it precipitated out and the reduction in biofilm inhibition was 20% (result not shown).

Here at least, there is a concentration dependence. Besides octyloxybutyrolactone (H128), octyloxypantolactone (H33) showed the best result (more than 30% biofilm reduction at 100 ppm). The other active substances (H99: butyloxybuty-rolactone; H123: butyloxypantolactone) showed only a moderate effect on biofilm formation. In all cases the cell growth was not destroyed.

For subsequent experiments, new, higher substance amounts and additional alkyloxylactone derivatives were synthesized (Table 1; FIG. 2). In order to eliminate secondary influences from solvents such as toluene or dichloromethane, for all compounds the quantity of residual solvent was determined by gas chromatography and in all cases fell in the lower limits of detection (purity >97% by GLC experiments).

After 6 hours incubation, differences in biofilm formation were observed for the DMSO control (set to 100% in FIG. 2) in comparison with the tests using various alkyloxylactones (Table 1). 100 ppm of each active substance were added to the starting materials. The test with 100 ppm heptylpantolactone (188) showed a biofilm reduction of more than 40% (with respect to the control). The pantolactone derivatives with a longer side chain at $R_3$ (Formula I) showed a lower effect on the biofilm formation with increasing length of side chain (FIG. 2, dark gray bars). For the butyrolactone derivatives (FIG. 2, dark gray bars), however, the compounds with longest side chains (hexadecylbutyrolactone) showed the best biofilm reduction, while the derivatives with shorter chains only produced a biofilm reduction of 20%. The educts hydroxybutyrolactone and pantolactone (FIG. 2, hatched bars) did not show any notable effect. In all investigated cases the cell growth was not destroyed, i.e. no biocidal effect was observed.

TABLE 1

Tested Alkoxylactone Derivatives.

| | |
|---|---|
| C8-Butyro | Heptyloxybutyrolactone |
| | Octyloxybutyrolactone |
| C13-Butyro | Tridecyloxybutyrolactone |
| C16-Butyro | Hexadecyloxybutyrolactone |
| C7-Panto | Heptyloxypantolactone |
| C8-Panto | Octyloxypantolactone |
| C13-Panto | Tridecyloxypantolactone |
| C16-Panto | Hexadecyloxypantolactone |
| K DMSO | DMSO-Control |
| E Butyro | Educt Hydroxybutyrolactone |
| E Panto | Educt Pantolactone |

The invention claimed is:

1. A compound of the formula I,

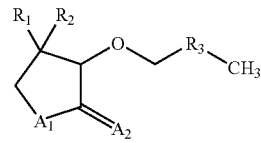

wherein $A_1$ is O or NH; $A_2$ is O or S; each of $R_1$ and $R_2$ is independently hydrogen, a methyl or $C_2$-$C_8$-saturated or mono- or doubly unsaturated, branched or linear hydrocarbon group or a $C_2$-$C_8$-saturated or mono- or doubly unsaturated, branched or linear hydrocarbon group comprised of an O and/or S atom in the chain wherein the hydrocarbon group is optionally mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl; $R_3$ is a $C_1$-$C_{18}$-saturated or mono or doubly unsaturated, branched or linear hydrocarbon group or a $C_1$-$C_{18}$-saturated or mono- or doubly unsaturated, branched or linear hydrocarbon group comprised of an O and/or S atom in the chain wherein the hydrocarbon group is optionally mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl; with the proviso that when each of $A_1$ and $A_2$ is O and each of $R_1$ and $R_2$ is hydrogen or methyl, $R_3$ is other than methylene or ethylene.

2. A compound of claim 1 wherein each of $A_1$ and $A_2$ is O; each of $R_1$ and $R_2$ is independently hydrogen or methyl, and $R_3$ is butylene, pentylene, hexylene, heptylene, octylene, nonylene, decylene, undecylene, dodecylene, tridecylene or tetradecylene.

3. A method for synthesizing a compound of claim 1 comprising reacting an appropriate lactone, lactam or thiolactam with a 1-haloalkane in an organic solvent and in the presence of a base.

4. A method of inhibiting quorum sensing by gram-negative bacteria comprising contacting a reaction medium comprised of the bacteria with a compound of the formula I,

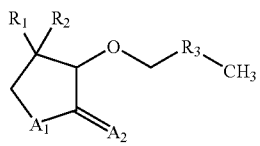

wherein $A_1$ is O or NH; $A_2$ is O or S; each of $R_1$ and $R_2$ is independently hydrogen, a methyl or $C_2$-$C_8$-saturated or mono- or doubly unsaturated, branched or linear hydrocarbon group or a $C_2$-$C_8$-saturated or mono- or doubly unsaturated, branched or linear hydrocarbon group comprised of an O and/or S atom in the chain wherein the hydrocarbon group can be mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl; $R_3$ is a $C_1$-$C_{18}$-saturated or mono- or doubly unsaturated, branched or linear hydrocarbon group or a $C_1$-$C_{18}$-saturated or mono- or doubly unsaturated, branched or linear hydrocarbon group comprised of an O and/or S atom in the chain wherein the hydrocarbon group can be mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl, wherein the compound is applied in an sufficient to inhibit the quorum sensing.

5. The method of claim 4 wherein the quorum sensing inhibited is the development and/or maturation of biofilms; multicellular swarm behavior; the concerted development of antibiotic resistances; the concerted synthesis of antibiotics; the concerted synthesis of pigments; the concerted production of extracellular enzymes; or the concerted production of virulence factors.

6. The method of claim 5 wherein the extracellular enzymes are hydrolytic enzymes.

7. A method for controlling the development and/or maturation of biofilms comprising contacting a reaction medium comprised of gram-negative bacteria with a compound of the formula I,

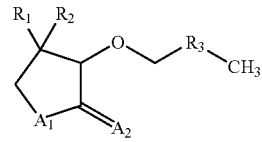

wherein $A_1$ is O or NH; $A_2$ is O or S; each of $R_1$ and $R_2$ is independently hydrogen, a methyl or $C_2$-$C_8$-saturated or mono- or doubly unsaturated, branched or linear hydrocarbon group or a $C_2$-$C_8$-saturated or mono or doubly unsaturated, branched or linear hydrocarbon group comprised of an O and/or S atom in the chain wherein the hydrocarbon group can be mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl; $R_3$ a $C_1$-$C_{18}$-saturated or mono- or doubly unsaturated, branched or linear hydrocarbon group or a $C_1$-$C_{18}$-saturated or mono- or doubly unsaturated, branched or linear hydrocarbon group comprised of an O and/or S atom in the chain wherein the hydrocarbon group can be mono- or multiply-substituted by a substituent selected from the group consisting of halogen, hydroxy, $C_1$-$C_6$-alkyl, trifluoromethyl, $C_1$-$C_6$-alkoxy, $C_6$-$C_{10}$-aryl, and $C_1$-$C_6$-alkyl-$C_6$-$C_{10}$-aryl, wherein the compound is added in an amount sufficient for controlling the development and/or maturation of biofilms.

8. The method of claim 7 wherein the biofilm is developed and/or matured in sterilization agents, disinfectants, impregnation agents, preservatives, detergents, cleansing agents, coolants or cooling lubricants.

9. The method of claim 7 wherein the biofilm is developed and/or matured in medical equipment, medical instruments, catheters or endoscopes.

10. The method of claim 7 wherein the amount of the compound of formula 1 is from 1 ppm to 1000 ppm.

11. The method of claim 10 wherein the amount of the compound of formula 1 is from 20 ppm to 500 ppm.

12. The method of claim 10 wherein the amount of the compound of formula 1 is from 20 ppm to 100 ppm.

13. A composition comprising a product selected from the group consisting of body care agents, hair shampoos, hair care agents, bubble baths, a shower bath, creams, gels, lotions, alcoholic and aqueous-alcoholic solutions, emulsions, wax/fatty masses, sticks, powders or salves, mouth-, tooth- or denture care products, cosmetics, detergents, cleansing agents, rinsing agents, hand detergents, hand dishwashing agents, automatic dishwasher agents, disinfectants, agents for treating foodstuffs, pharmaceuticals, filter media, textiles, hides, paper, skins and leather and a compound of claim 1.

* * * * *